US012778974B2

(12) United States Patent
Niu et al.

(10) Patent No.: US 12,778,974 B2
(45) Date of Patent: Nov. 3, 2026

(54) APPLICATION OF NARINGIN COMBINED WITH RAPAMYCIN IN PREPARATION OF MEDICATIONS FOR TREATING HYPERLIPIDEMIA

(71) Applicant: AIR FORCE MEDICAL UNIVERSITY, Xi'an (CN)

(72) Inventors: Lina Niu, Xi'an (CN); Kaiyan Wang, Xi'an (CN); Weiwei Yu, Xi'an (CN); Wen Qin, Xi'an (CN); Yuxuan Ma, Xi'an (CN); Chen Lei, Xi'an (CN)

( * ) Notice: Subject to any disclaimer, the term of this patent is extended or adjusted under 35 U.S.C. 154(b) by 404 days.

(21) Appl. No.: 18/398,851

(22) Filed: Dec. 28, 2023

(65) Prior Publication Data

US 2024/0122956 A1 Apr. 18, 2024

(51) Int. Cl.

*A61K 31/7048* (2006.01)
*A61K 31/436* (2006.01)
*A61P 3/06* (2006.01)

(52) U.S. Cl.

CPC ........ *A61K 31/7048* (2013.01); *A61K 31/436* (2013.01); *A61P 3/06* (2018.01)

(58) Field of Classification Search

USPC ........................................................ 514/27
See application file for complete search history.

(56) References Cited

PUBLICATIONS

Pu et al., Archives of Biochemistry and Biophysics, vol. 518, 2012, pp. 61-70. (Year: 2012).*
Pengnet et al., BioMed Research International, vol. 2019, article ID 3708497, pp. 1-11. (Year: 2019).*

* cited by examiner

*Primary Examiner* — Traviss C Mcintosh, III

(57) ABSTRACT

The present disclosure relates to the field of medicine and specifically to an application of naringin combined with rapamycin in preparation of medications for treating hyperlipidemia. Naringin achieves anti-inflammatory and lipid-lowering effects by inhibiting the formation of oxLp-NLRP3 complexes. The present disclosure has been substantiated through cellular experiments and animal experiments, it demonstrates that naringin effectively intervenes in the early progression of hyperlipidemia by neutralizing oxLp and inhibiting the formation of oxLp-NLRP3 complexes. The inhibitory effect of naringin on oxLp-NLRP3 complexes contributes to unleashing the therapeutic potential of rapamycin in hyperlipidemia, providing a combined strategy for the prevention and treatment of hyperlipidemia-related diseases in clinical applications. Furthermore, this oxLp-targeted treatment strategy avoids interference with the protective immune function of NLRP3 and serves as a theoretical basis for the prevention and treatment of other oxLp-related disorders.

6 Claims, 10 Drawing Sheets

APPLICATION OF NARINGIN COMBINED WITH RAPAMYCIN IN PREPARATION OF MEDICATIONS FOR TREATING HYPERLIPIDEMIA

CROSS-REFERENCE TO RELATED APPLICATION

This application claims priority to Chinese Patent Application No. 202311447468.0, filed on Nov. 2, 2023 before the China National Intellectual Property Administration, the disclosure of which is incorporated herein by reference in entirety.

TECHNICAL FIELD

The present disclosure relates to the field of medicine, and in particular to an application of naringin combined with rapamycin in preparation of medications for treating hyperlipidemia.

BACKGROUND

Hyperlipidemia is a significant public health issue closely associated with various diseases such as cardiovascular disease, non-alcoholic fatty liver disease, osteoporosis, and tumor. Lipid accumulation and chronic inflammatory reaction often coexist and mutually influence each other, accelerating the development of diseases related to hyperlipidemia. Therefore, targeted interventions focusing on lipid accumulation and inflammatory reaction are crucial for the clinical treatment of hyperlipidemia-related diseases. During the development of hyperlipidemia, oxidized lipoproteins (oxLp), particularly oxidized low-density lipoprotein (oxLDL), are considered as a main factor of triggering lipid accumulation and inflammatory reactions. NOD-like receptor thermal protein (pyrin) domain associated protein 3 (NLRP3), as an intracellular pattern recognition receptor, can perceive the accumulation of oxLDL inside cells, and bind to the downstream apoptosis-associated speck-like protein (ASC), and subsequently recruit pro-caspase-1 and then aggregate into NLRP3 inflammasome. The activated NLRP3 inflammasome cleaves pro-caspase-1 into active caspase-1, which then promotes the maturation and release of the inflammatory factor IL-1β and induces inflammatory responses. Previous studies by the applicant indicate that under oxLp stimulation, NLRP3 aggregates and activates on oxLp, triggering the formation of oxLp-NLRP3 complexes. These stable complexes resist autophagic degradation, resulting in the continuous accumulation of oxLp and over-activation of NLRP3, subsequently causing sustained intracellular lipid accumulation and inflammatory reaction. This discovery provides new insights into targeted therapies for hyperlipidemia-related diseases.

Therefore, the present disclosure aims to intervene in lipid accumulation and inflammatory reaction by inhibiting the formation of oxLp-NLRP3 complexes, offering an effective strategy for treating hyperlipidemia-related diseases.

SUMMARY

To address the aforementioned issues in the existing technology, the present disclosure discloses an application of naringin combined with rapamycin in preparation of medications for treating hyperlipidemia.

According to some embodiments of the present disclosure, the naringin inhibits the formation of oxLp-NLRP3 complexes, achieving anti-inflammatory and lipid-lowering effects. The oxLp-NLRP3 complex is formed by the aggregation and activation of NOD-like receptor thermal protein (pyrin) domain associated protein 3 (NLRP3) on oxidized lipoproteins.

According to some embodiments of the present disclosure, the rapamycin is used to enhance the efficacy of naringin. Rapamycin, also known as sirolimus, is a macrocyclic lactone antibiotic immunosuppressive agent. Clinically, it is used for anti-rejection in organ transplantation and treatment of autoimmune diseases. It exhibits immunosuppressive activity tens of times stronger than the widely used cyclosporine, with low toxicity and a small dosage (2 mg/day/person), it exhibits synergistic immunosuppressive effects when used in combination with cyclosporine clinically. Compared to cyclosporine and FK506 (tacrolimus), sirolimus has the lowest renal toxicity among other immunosuppressive agents and no neurotoxicity.

According to some embodiments of the present disclosure, the anti-inflammatory effect includes inhibiting the activation of NLRP3 inflammasomes and the release of downstream inflammatory factor IL-1β.

According to some embodiments of the present disclosure, in hyperlipidemic mice, the regulatory effects on lipid accumulation and inflammatory reaction are not significant when rapamycin is used alone. However, when used in combination with naringin, it exhibits a significant reduction in lipid accumulation and inflammatory reaction.

Based on the concept of the present disclosure mentioned above, a combination medication for treating hyperlipidemia is provided, comprising naringin and rapamycin as active ingredients.

According to some embodiments of the present disclosure, naringin and rapamycin are administered simultaneously or consecutively.

According to some embodiments of the present disclosure, the combination medication includes a pharmaceutically acceptable carrier.

The pharmaceutically acceptable carrier comprises conventional diluents (such as injection water, microcrystalline cellulose, etc., at least one type), fillers (such as mannitol, sucrose, lactose, polyethylene glycol, Tween 80, sorbitol, menthol, liquid paraffin, vaseline, stearic acid, glyceryl monostearate, lanolin, mineral oil, DMSO, at least one type), binders (such as carbomer, gum arabic, starch, cellulose, gelatin, polyvinyl pyrrolidone, polyacrylamide, at least one type), disintegrants (such as sodium carboxymethyl starch, crosslinked sodium carboxymethyl cellulose, hydroxypropyl cellulose, low-substituted hydroxypropyl cellulose, at least one type), lubricants (such as talc, magnesium stearate, calcium stearate, solid polyethylene glycol, lecithin, silicon dioxide, micronized silica gel, at least one type), wetting agents (such as propylene glycol, glycerol, ethanol, at least one type), stabilizers (such as disodium ethylenediaminetetraacetate, sodium thiosulfate, sodium metabisulfite, sodium sulfite, sodium bisulfite, ethanolamine, sodium bicarbonate, sodium acetate, niacinamide, vitamin C, at least one type), osmotic pressure regulators (such as sodium chloride, glucose, at least one type), pH regulators (such as triethanolamine, sodium hydroxide, sodium citrate, at least one type), preservatives (such as trichlorobutanol, methylparaben, hydroxyethyl ester, benzalkonium bromide, at least one type). The above-mentioned excipients may be in commonly used doses and mixed with naringin and rapamycin in commonly used ratios. After the dosage of naringin and rapamycin is determined, the ratio of pharmaceutical excipients to each other may be adjusted appropriately as needed.

According to some embodiments of the present disclosure, the dosage forms of the combination medication include oral dosage forms and non-gastrointestinal administration dosage forms.

According to some embodiments of the present disclosure, the oral dosage form specifically includes granules, tablets, capsules, pills, pellets, or oral liquid formulations.

According to some embodiments of the present disclosure, the non-gastrointestinal administration dosage form specifically includes injectable dosage forms.

In a specific embodiment of the present disclosure, naringin is administered in the form of an injectable preparation, rapamycin is administered in the form of capsules, and the rapamycin capsules are added to the diet simultaneously with the injection of naringin.

The present disclosure has beneficial effects:

The research results of the present disclosure demonstrate that naringin inhibits the formation of oxLp-NLRP3 complexes by neutralizing oxLp, effectively intervening in the early progression of hyperlipidemia. The inhibition of oxLp-NLRP3 complexes by naringin helps unleash the therapeutic potential of rapamycin in hyperlipidemia, providing a combined strategy for the prevention and treatment of hyperlipidemia-related diseases in clinical practice. Additionally, this oxLp-directed (oxLp-targeted) treatment strategy avoids interfering with the protective immune function of NLRP3 and provides a theoretical basis for the prevention and treatment of other oxLp-related diseases.

DETAILED DESCRIPTION OF EMBODIMENTS

The following detailed description of the present disclosure is provided in conjunction with the accompanying drawings and specific embodiments. However, it should not be construed as limiting the scope of the present disclosure. Unless otherwise specified, the technical means used in the following embodiments are conventional means known to those skilled in the art, and the materials, reagents, etc., used in the following embodiments, if not specifically specified, can be obtained from commercial sources.

The preliminary research of the present disclosure found that intracellular abnormally-distributed oxLp, as an endogenous ligand, triggers the recruitment (aggregation) and activation of NLRP3, forms stable complexes with activated NLRP3, thereby driving the continuous accumulation of oxidized lipids and overactivation of NLRP3 inflammasomes. This unregulated process of lipid accumulation and inflammatory reaction, induced by oxLp-NLRP3 complexes, accelerates the progression of hyperlipidemia. Considering the role of oxLp-NLRP3 complexes in the progression of hyperlipidemia, a drug screening technique was employed to search for potential compounds among 200 natural products with the aim of neutralizing oxLp. The results showed that naringin has high affinity for oxidized low-density lipoprotein (oxLDL) and oxidized high-density lipoprotein (oxHDL), it is capable of neutralizing the negative charge on the surfaces of oxLDL and oxHDL. Therefore, naringin was selected for further investigation.

Embodiment 1: Inhibitory Effect of Naringin on the Formation of oxLp-NLRP3 Complexes in THP-1 Cells Cell Culture and Treatment: THP-1 cells (from American Type Culture Collection, Manassas, Virginia) were cultured in RPMI 1640. They were pre-treated with naringin (Sigma, 91842; 100 μM) for 1 hour, followed by cultivation in serum-free medium containing oxLDL and oxHDL (50 μg/mL) for 3 hours. The culture condition was maintained at 37° C. and with 5% $CO_2$.

Measurement of Intracellular Cholesterol: Intracellular cholesterol was determined using a commercially available intracellular cholesterol assay kit according to the manufacturer's instructions.

Measurement of IL-1β: IL-1β was measured using a commercially available IL-1β assay kit according to the manufacturer's instructions.

Figure 1:
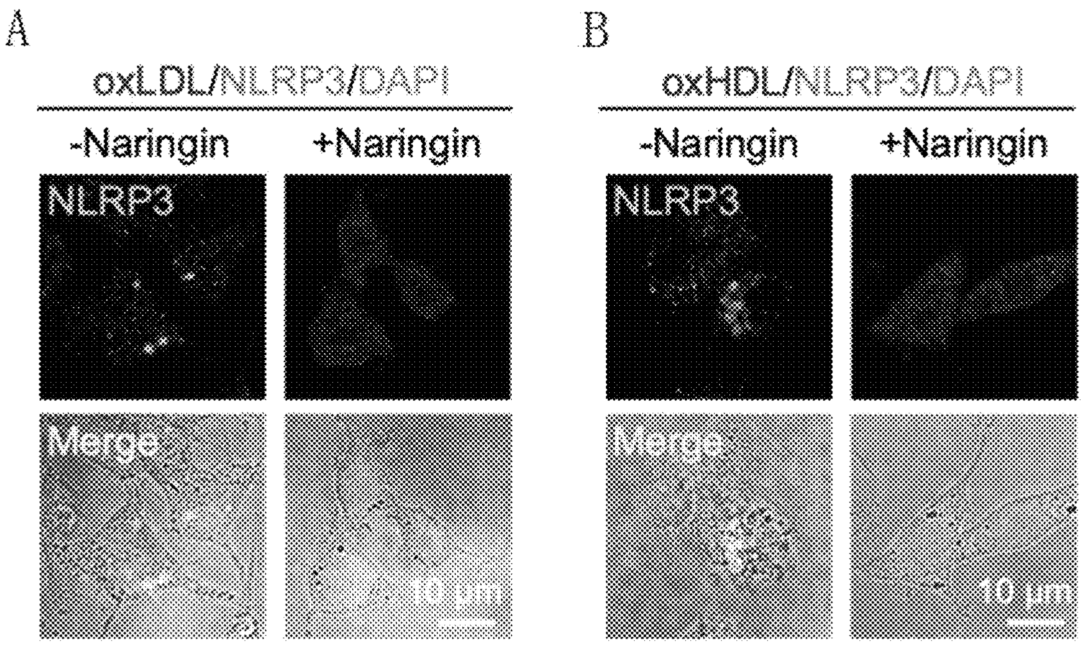
FIG. 1 shows the fluorescence imaging results of oxLDL-NLRP3 complexes (A) and oxHDL-NLRP3 complexes (B) after treatment with naringin.
Figure 2:
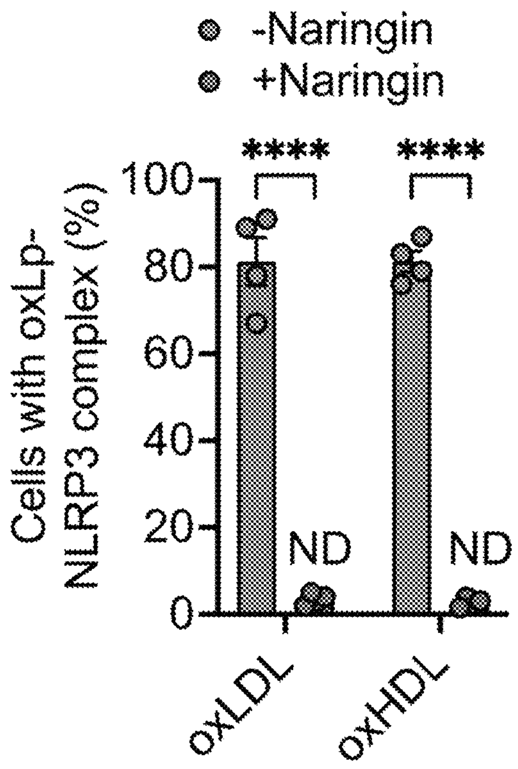
FIG. 2 shows the proportions of oxLDL-NLRP3 complexes and oxHDL-NLRP3 complexes in THP-1 cells.
Figure 3:
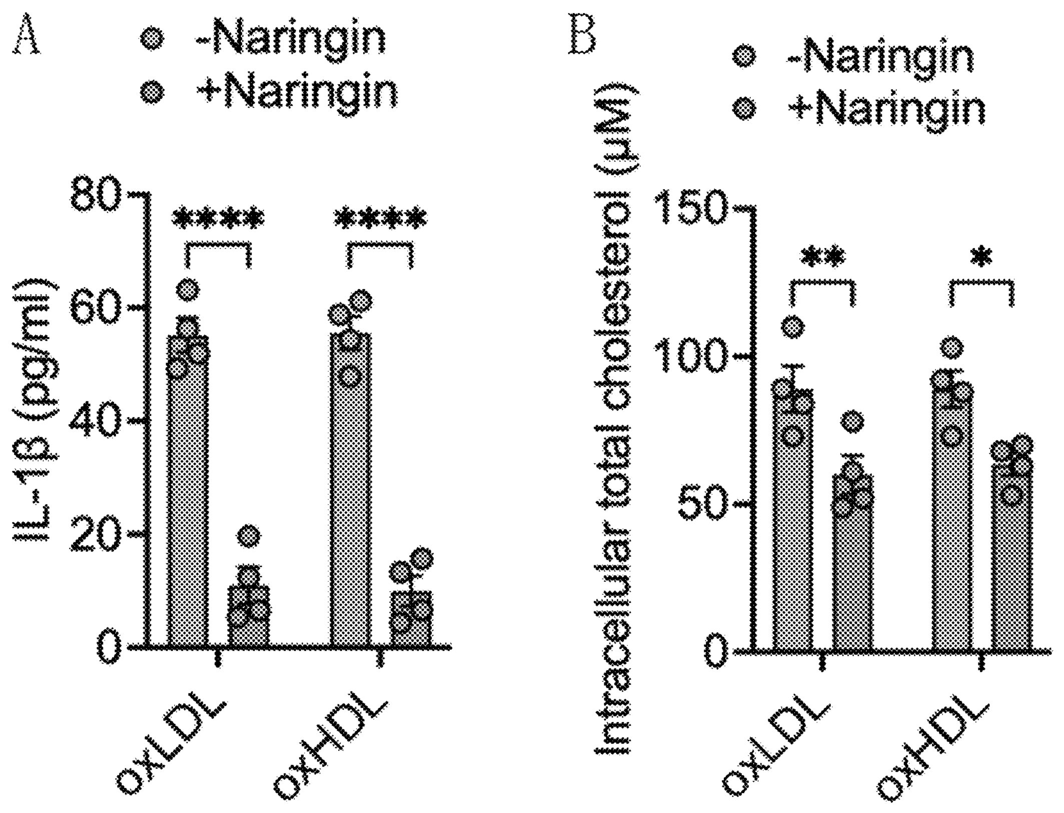
FIG. 3 shows the levels of IL-1β release (A) and intracellular cholesterol accumulation (B) in THP-1 cells treated with naringin.

Results: In THP-1 cells, pre-treatment with naringin inhibited the formation of complexes between oxLDL or oxHDL and NLRP3 (FIG. 1, FIG. 2). In cells pre-treated with naringin, oxLDL- or oxHDL-induced IL-1β release and cholesterol accumulation were simultaneously reduced (FIG. 3).

Figure 4:
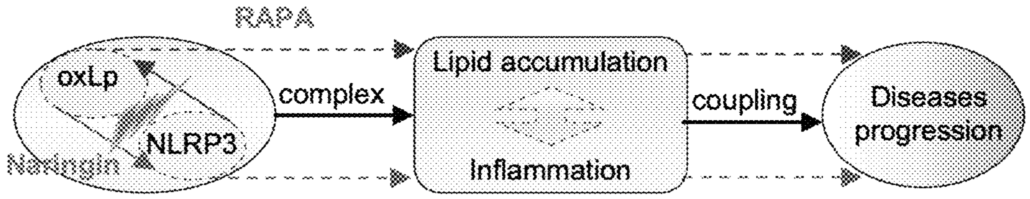
FIG. 4 is a schematic diagram showing the mechanism of action of naringin-rapamycin combination therapy for hyperlipidemia.
Figure 5:
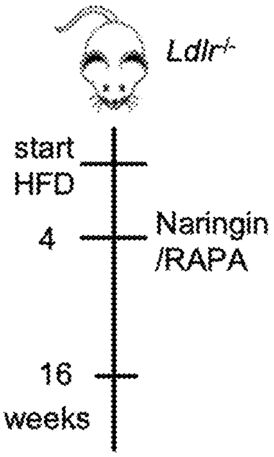
FIG. 5 shows the construction of a mouse hyperlipidemia model and the process of drug intervention.

Embodiment 2: Combined Treatment of Naringin and Rapamycin (*RAPA*) for Hyperlipidemia To evaluate the synergistic therapeutic effects of naringin and rapamycin on hyperlipidemia mice (FIG. 4), a hyperlipidemia model was established using $Ldr1^{-/-}$ (C57BL/6J) mice. $Ldr1^{-/-}$ mice were fed with a high-fat diet (HFD) from 4 weeks of age for 16 weeks, received daily intraperitoneal injections of naringin (20 mg/kg) and active capsule rapamycin (*RAPA,* 40 mg/kg) added to the diet, as shown in FIG. 5. Subsequently, mouse serum, tissues of carotid arteries, liver, and aortic root were collected for analysis.

Assessment of Lesions in Carotid Arteries, Aortic Roots, and Liver Tissues: Carotid arteries, hearts, and livers of mice were dissected, fixed overnight with 4% PFA, and carotid arteries were stained with Oil Red O after gently removing adherent (outer membrane) fat and flattening them from the carotid arteries. The stained aortas were placed on anti-falloff slides, fully unfolded, and images were captured using a high-resolution camera. Hearts and livers were embedded in OCT tissue, and 7-10 μm thick continuous sections were collected. Staining was performed with Oil Red O and hematoxylin and eosin. Stained sections were analyzed using an optical microscope. ImageJ (version 2.10) was used for quantitative analysis of the images. Lesion areas were assessed according to the percentage of Oil Red 0-positive areas in the total sampled area.

Figure 6:
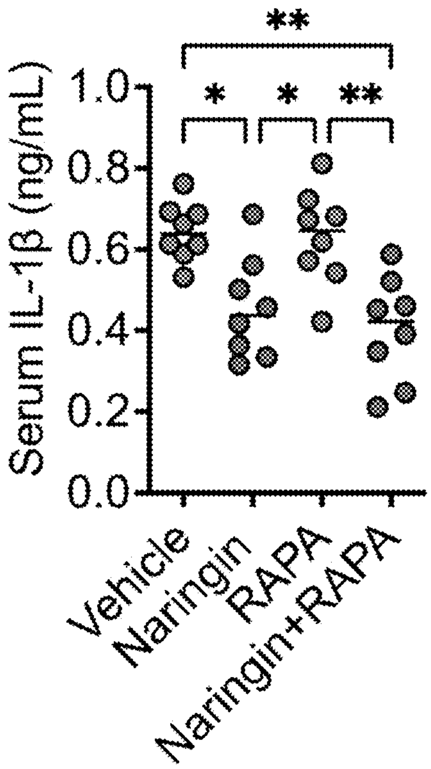
FIG. 6 shows the detection results of serum IL-1β in mice after naringin-rapamycin combination therapy.
Figure 7:
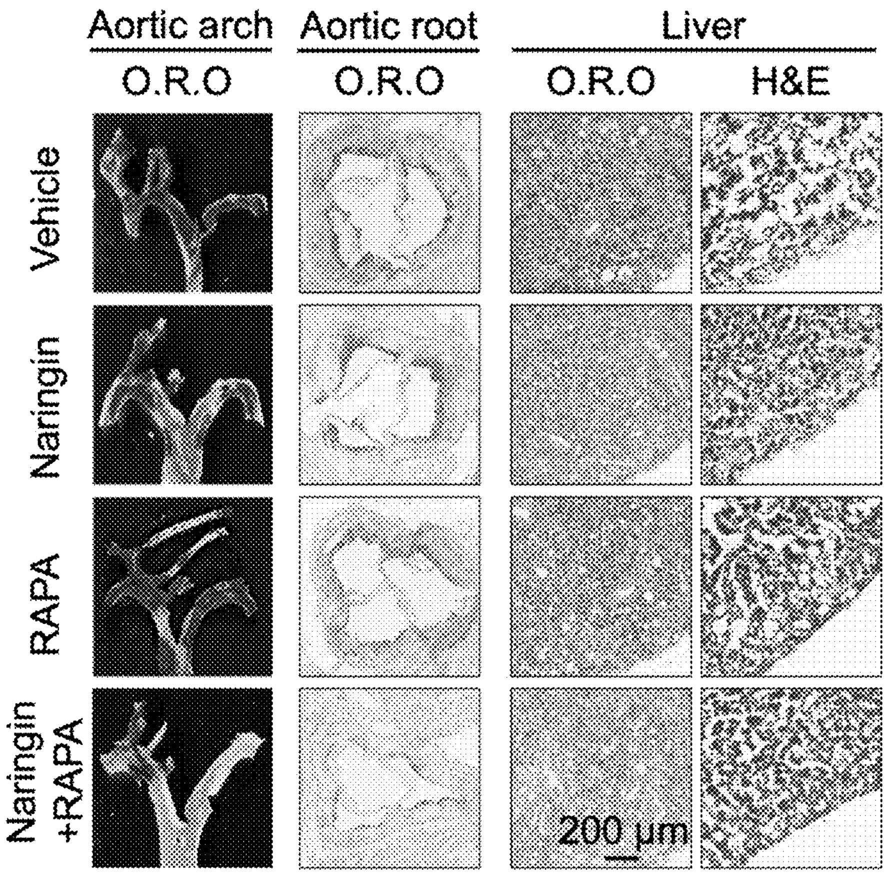
FIG. 7 shows the arterial plaques, aortic root, and liver lesions in mice after naringin-rapamycin combination therapy.
Figure 8:
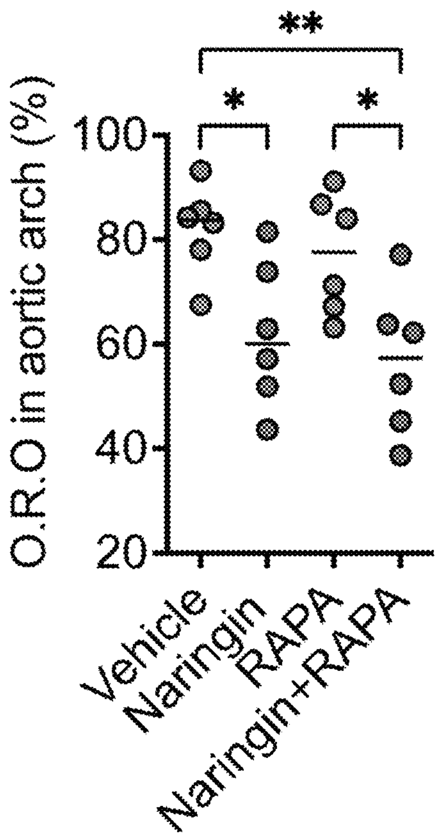
FIG. 8 shows the percentage of arterial plaque area to the total surface area of the aortic arch, as stained with O.R.O.
Figure 9:
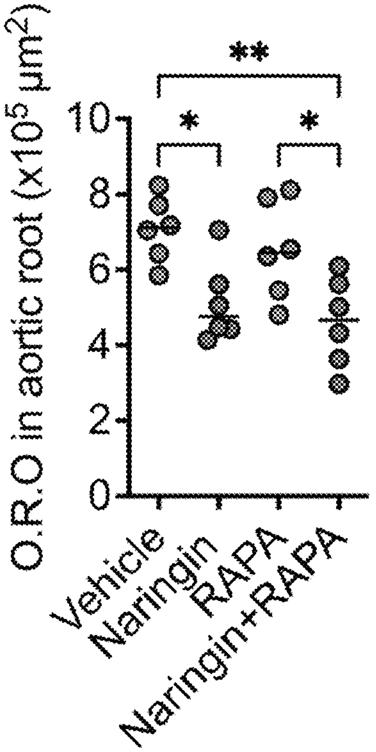
FIG. 9 shows the percentage of lesion area in the aortic root to the total sampled area of the aortic root, as stained with O.R.O.
Figure 10:
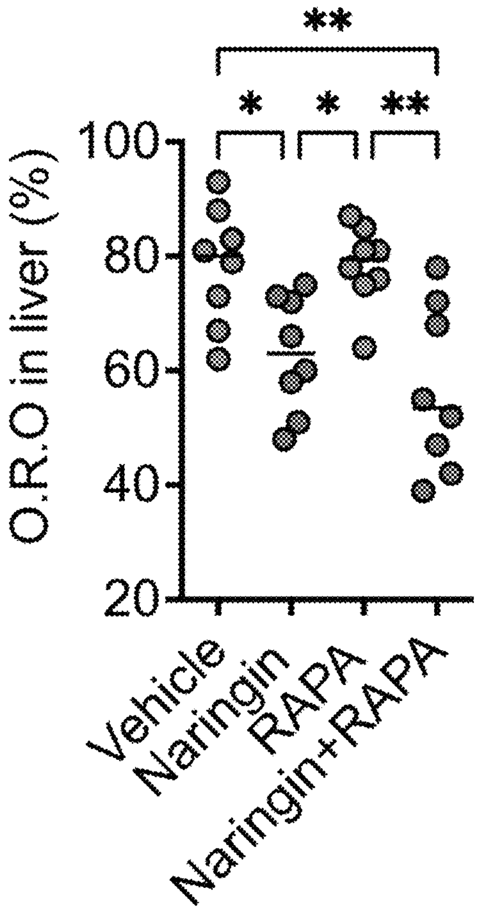
FIG. 10 shows the percentage of liver lipid accumulation area to the total sampled area of the liver, as stained with O.R.O.

Results: As shown in FIG. 6, serum analysis showed that in hyperlipidemic mice, single treatment with rapamycin had no significant regulatory effect on IL-1β, but when used in combination with naringin, there was a significant reduction in IL-1β release. Furthermore, naringin treatment alleviated lipid accumulation in the carotid arteries, aortic roots, and livers of hyperlipidemic mice, and when used in combination with rapamycin, the therapeutic effect was significantly enhanced (FIGS. 7-10).

The above results indicate that naringin exerts a dual effect of anti-inflammatory and lipid-lowering by inhibiting the formation of oxLp-NLRP3 complexes, and when used in combination with rapamycin, it synergistically intervenes in the progression of hyperlipidemia.

Although optional embodiments of the present disclosure have been described, those skilled in the art may make additional changes and modifications to these embodiments once they have knowledge of the basic inventive concepts. Therefore, the appended claims are intended to include all such changes and modifications that fall within the scope of the present disclosure.

Obviously, those skilled in the art can make various changes and modifications to the present disclosure without departing from the spirit and scope of the present disclosure. Thus, if these modifications and variations of the present disclosure fall within the scope of the claims and their equivalents, the present disclosure is intended to include these modifications and variations.

What is claimed is:

1. A method for treating hyperlipidemia comprising administering effective amounts of naringin and rapamycin, wherein the rapamycin is used to enhance an efficacy of the naringin, wherein the naringin is administered in a form of an injectable preparation, the rapamycin is administered in a form of capsules and rapamycin capsules are added to a diet simultaneously with the injection of naringin, wherein the naringin inhibits a formation of oxLp-NLRP3 complexes by neutralizing oxLp, achieving anti-inflammatory and lipid-lowering effects by disrupting the formation of oxLp-NLRP3 complexes, wherein the anti-inflammatory effect comprises inhibiting activation of NLRP3 inflammasomes and release of downstream inflammatory factor IL-1β, wherein the oxLo-NLRP3 complexes resist autophagic degradation, resulting in the continuous accumulation of oxLp and overactivation of NLRP3, subsequently causing sustained intracellular lipid accumulation and inflammatory reaction, wherein the naringin and the rapamycin when used in combination, exhibit a reduction in lipid accumulation and inflammatory reaction, and wherein oxLDL- or oxHDL-induced IL-18 release and cholesterol accumulation are simultaneously reduced.

2. The method according to claim 1, wherein the naringin and rapamycin are active ingredients of a combination medication for treating hyperlipidemia.

3. The method according to claim 2, wherein the combination medication further comprises a pharmaceutically acceptable carrier.

4. The method according to claim 3, wherein a dosage form of the combination medication comprises an oral dosage form and a non-gastrointestinal administration dosage form.

5. The method according to claim 4, wherein the oral dosage form comprises granules, tablets, capsules, pills, pellets, or oral liquid formulations.

6. The method according to claim 4, wherein the non-gastrointestinal administration dosage form comprises an injectable dosage form.

* * * * *